United States Patent [19]
Cohen et al.

[11] 3,936,164
[45] Feb. 3, 1976

[54] INSTRUMENTS FOR MEASURING VISUAL FIELDS

[75] Inventors: Samuel W. Cohen, Brooklyn; Anton Banko, Bronx, both of N.Y.

[73] Assignee: Surgical Design Corporation, Long Island City, N.Y.

[22] Filed: Feb. 3, 1975

[21] Appl. No.: 546,404

Related U.S. Application Data

[63] Continuation of Ser. No. 273,150, July 19, 1972, abandoned.

[52] U.S. Cl. .................. 351/23; 350/96 B; 351/36; 351/158
[51] Int. Cl.² .................... A61B 3/02; G02B 5/16
[58] Field of Search .............. 351/23, 24, 36, 158; 350/96 B

[56] References Cited
UNITED STATES PATENTS
3,482,905  12/1969  Ben Tovim ........................... 351/23

FOREIGN PATENTS OR APPLICATIONS
1,392,775  2/1965  France ................................. 351/23
  337,788  11/1930  United Kingdom .................. 351/23

*Primary Examiner*—Paul A. Sacher
*Attorney, Agent, or Firm*—Darby & Darby

[57] ABSTRACT

Instruments for measuring visual fields including a portable perimeter having a handle by which it can be held by the subject being tested. In a preferred embodiment, the perimeter includes a protractor which can be rotated clockwise-counterclockwise about an antero-posterior axis to any desired meridian. One end of a cord is attached to the protractor and a light source is attached to the other end of the cord. The protractor has angular markings thereon and the examiner uses the relationship of the cord to the angular marks and the meridian orientation of the protractor to determine the response of the eye to the light source. The protractor also can be rotated anteroposteriorly about a horizontal axis so that the same perimeter can be used to measure the response of both eyes merely by turning it over. A marking pad is provided to or upon which the response of a patient can be indicated when viewing the light source as it is moved through various angles of the field. In another embodiment of the invention, the angular field to be viewed is located on a chart held at a fixed distance from the perimeter and a light source is moved in front of or behind the chart.

27 Claims, 15 Drawing Figures

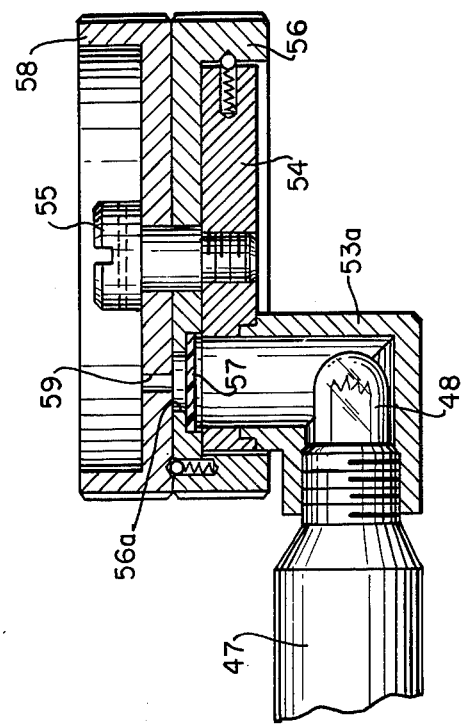
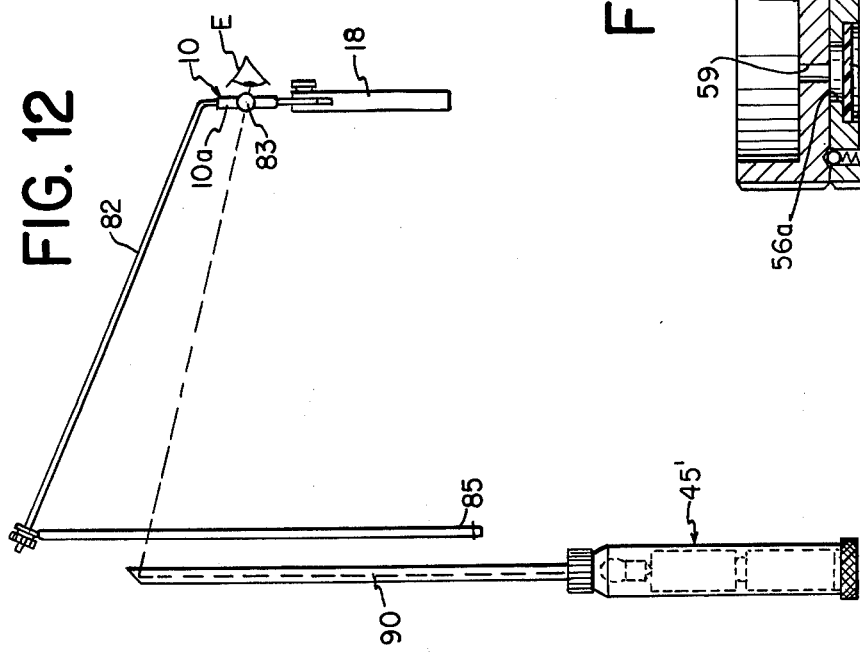
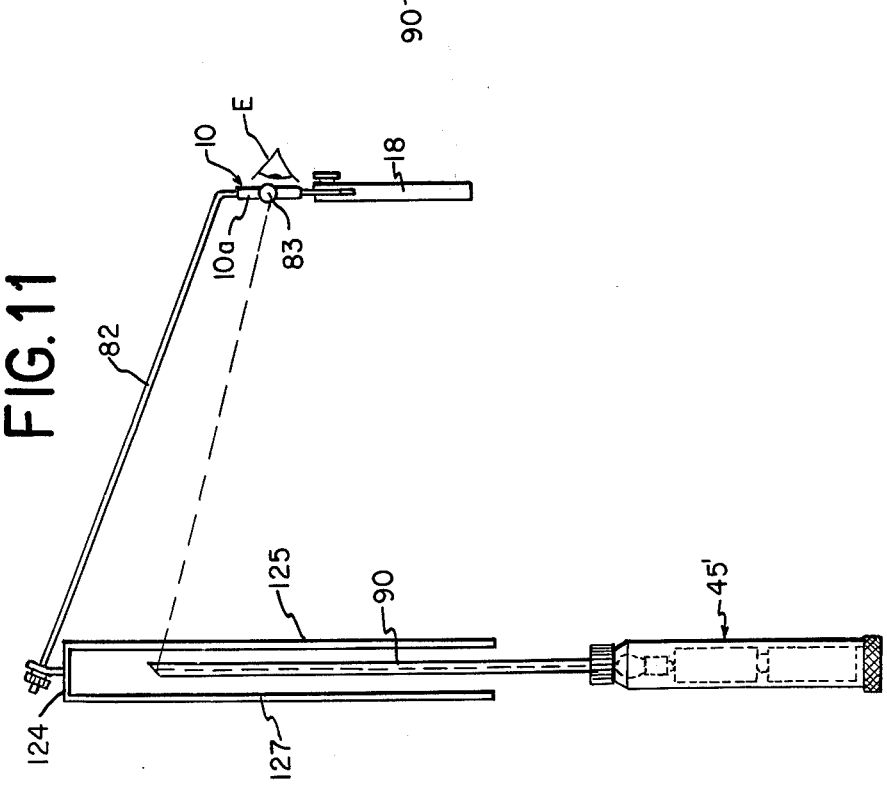

INSTRUMENTS FOR MEASURING VISUAL FIELDS

This is a continuation of application Ser. No. 273,150 filed July 19, 1972 and now abandoned.

An instrument generally known as a perimeter is currently available for quantitatively measuring the visual field response of the eye of a human patient. Such instruments are relatively large, heavy and complex in nature, are not easily portable and are also relatively expensive. Consequently, instruments are not readily available for use by persons who must make these measurements at a patient's bedside or at their home.

The present invention relates to lightweight, portable instruments for measuring the visual field response of the eye of a human patient. These instruments can be carried in one's pocket, and used also, just as large perimeters, for strabismometry for measurement of angle $\kappa$, for motor field monocular rotation measurements, and also to determine the location of retinal tears.

The preferred embodiment of the present invention is directed to a perimeter instrument which is relatively simple in construction and is also relatively inexpensive to manufacture and easy to operate. The perimeter comprises a frame, in the general shape of a pair of spectacles, and a handle for holding the frame. One of the open eye-pieces of the frame has inscribed therearound angular meridian markings. A protractor is mounted in the one frame opening and has angular scale markings inscribed thereon. The protractor is rotatable within the opening about a central support so that it can be aligned at any angular position (meridian) with respect to the frame. A cord of predetermined length is attached to the protractor support plane of the center of the one frame opening and an object, preferably in the form of a light source, is attached at the end of the cord. A pad of printed visual field charts is mounted on the other portion of the frame, where the second opening would normally be located. The person being examined orally, or otherwise, indicates his view of the light source as the examiner moves the source. The rotational location of the perimeter sets the meridian and the location of the cord with respect to the angle markings on the protractor gives the angle of view at the particular meridian. This information is recorded on the field chart.

The protractor can be moved through the frame opening so that the same perimeter can be used to measure the response of both eyes. Also, the field charts are made so that a mirror image of the recorded information appears, giving subjective response of the patient.

In accordance with other embodiments of the invention, a screen having a visual field pattern printed thereon is held at a fixed distance from the perimeter frame held by the patient. The examiner moves a light source with respect to the screen and the patient indicates his response which is recorded on a chart.

The instruments of the subject invention are relatively simple in construction. However, they operate successfully and accurately and are capable of making measurements heretofore capable of being made only by much larger and more costly instruments.

It is therefore an object of the invention to provide a relatively simple perimeter instrument for making various measurements of the eye of a human being.

It is an additional object to provide a pocket perimeter in the general shape of a pair of spectacles in which a moving light source is held at a fixed distance from the perimeter and the position of the light source with respect to the eye of the patient is readily determined.

An additional object is to provide a campimeter in which a screen having a field of view pattern printed thereon is held at a fixed distance from the eye of the patient being examined.

Other objects and advantages of the present invention will become more apparent upon reference to the following specification and annexed drawings, in which:

FIGS. 11 and 12 are elevational views showing modifications of the embodiment of instrument of FIG. 8; and FIG. 13 is an elevational view, partly in cross-section, of a portion of another embodiment of light source.

Figure 2:
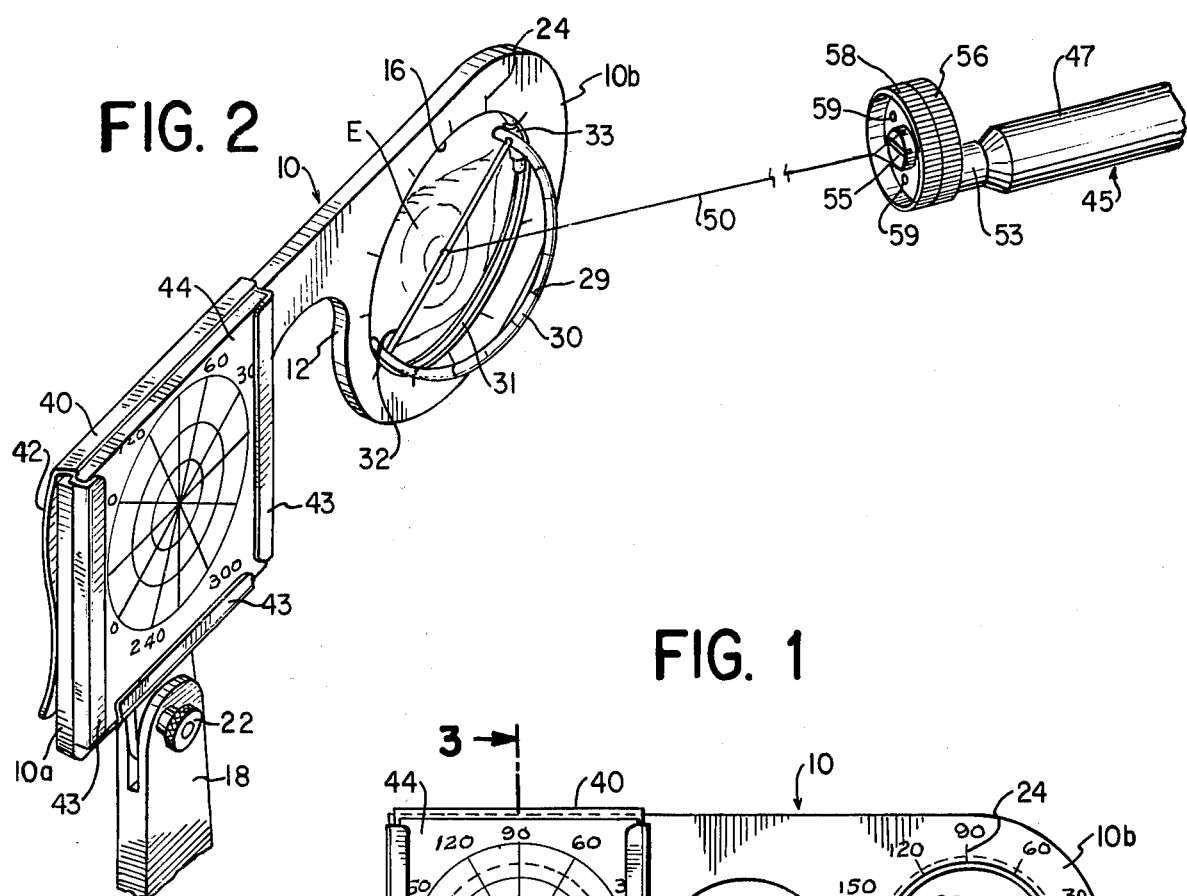
FIG. 2 is a perspective view of a portion of the instrument shown in use with respect to an eye.
Figure 1:
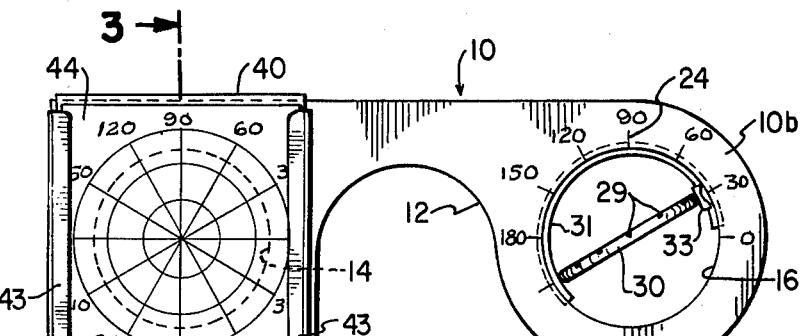
FIG. 1 is an elevational view of a portion of the instrument.
Figure 3:
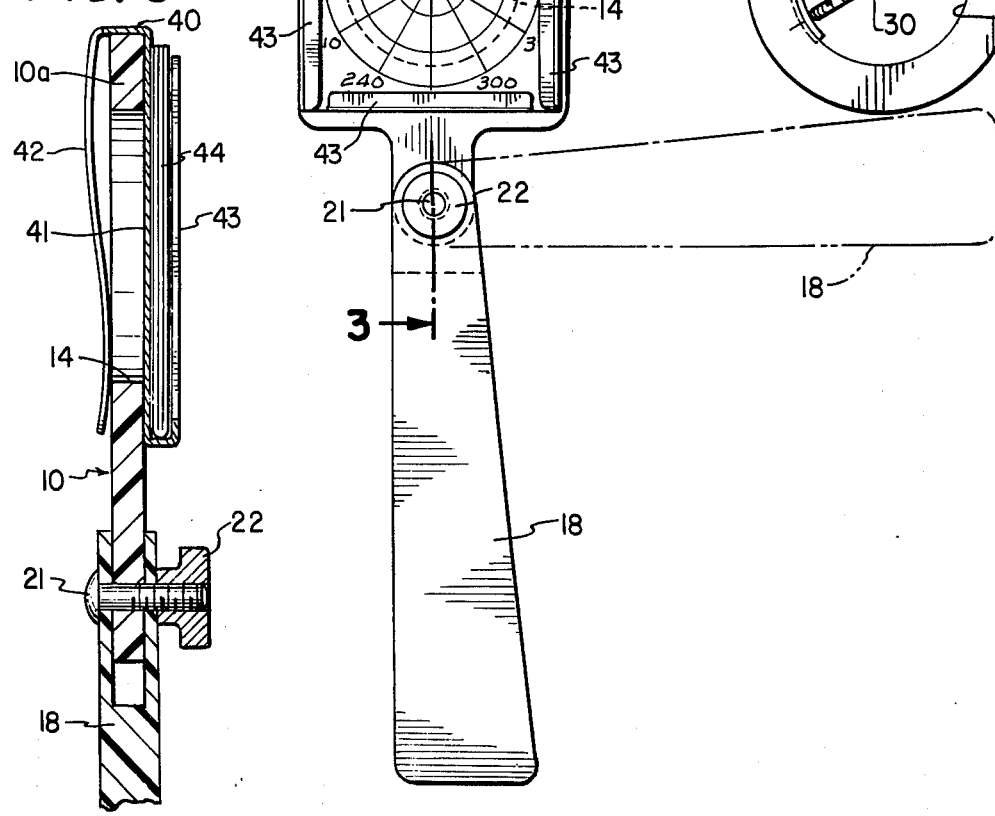
FIG. 3 is a side view of a portion of the instrument taken in cross-section along lines 3—3 of FIG. 1.

Referring first to FIGS. 1–3, the preferred embodiment of perimeter instrument of the present invention includes a frame 10 which can be of any suitable material, for example, transparent or opaque plastic, or of metal. Frame 10 is formed in the general shape of a pair of spectacles and has a central opening 12 formed for the nose of a patient being examined to protrude therethrough. One side of the frame 10a is generally rectangular in shape and has an opening 14 therein. The other side of the frame 10b is partially circular in form and has an opening 16 therein. A handle 18 is pivotally mounted to the frame portion 10a on a threaded screw 21 which has a lock nut 22. When the handle 18 is rotated to any suitable position, tightening the nut 22 will hold it in there. As shown in FIG. 1, the handle 18 can be moved from the unfolded position to a folded position shown in phantom lines. Thus, the perimeter instrument can be made quite compact when not in use and is only slightly larger than a pair of spectacles.

Frame portion 10b has a number of inscribed angular marks 24, corresponding to meridian lines, about the opening 16. The angle markings 24 are preferably made 30° apart although, of course, any suitable angular spacing can be utilized. It is also preferred that the top central marking be 90° and that the angular markings increase to 180° in a counter-clockwise direction and decrease to 0° in the clockwise direction, as shown in FIG. 1. For reasons to be described below, these angle markings 24 are placed on both sides of the frame.

Figure 4:
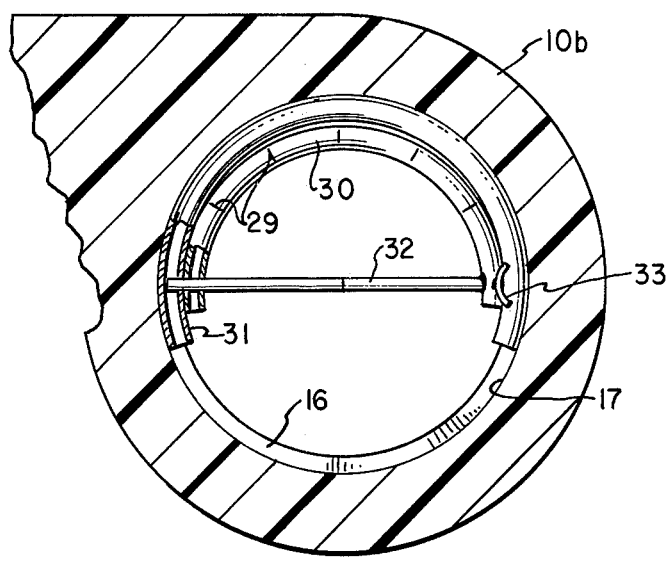
FIG. 4 is a plan view partly in cross-section and partly broken away, showing the details of the protractor and its mounting arrangement.
Figure 5:
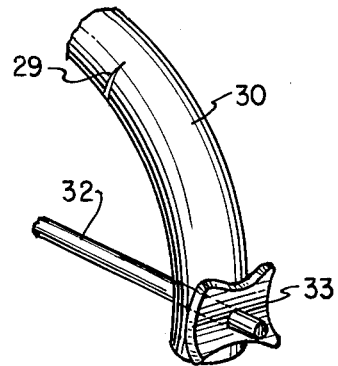
FIG. 5 is a fragmentary view showing a detail of the protractor mounting arrangement.

A protractor 30 is mounted to rotate with respect to the opening 16. The protractor is of rigid material and has a number of angle markings 29 inscribed thereon. The rotatable mounting for the protractor includes a generally semi-circular hollow ring 31 of rigid but springy material which is located within a groove 17 formed between the front and rear faces of the frame section 10b (See FIGS. 4 and 5). A cross-piece 32, which is also of rigid material, passes through the opposite ends of protractor 30. The ends of cross-piece 32 are positioned within the hollow mounting ring 31 and a spring washer 33 is located on one end of cross-piece 32 between protractor 30 and ring 31. A similar spring washer arrangement also can be provided, if desired, at each end of the cross-piece. This mounting arrangement leaves protractor 30 free to rotate a full 360° about cross-piece 32 with the spring or springs 33 permitting the protractor to be held in any desired plane. Further, the mounting ring 31 has spring characteristics and is also sized with respect to groove 17 so that the entire protractor assembly can be turned to align the protractor cross-piece 32 with any angle of the meridian markings 24 and held there.

A record chart holder 40 is mounted on spectacle frame section 10a. Holder 40 includes a base 41 having a spring clip-back portion 42. A lip 43 is formed on three sides of base 41 so that a plurality of single charts 44, or a pad of charts, can be slid and held within the lip. As should be apparent, the record holder 40 can be easily pulled off frame section 10a and its position reversed.

Figure 7:
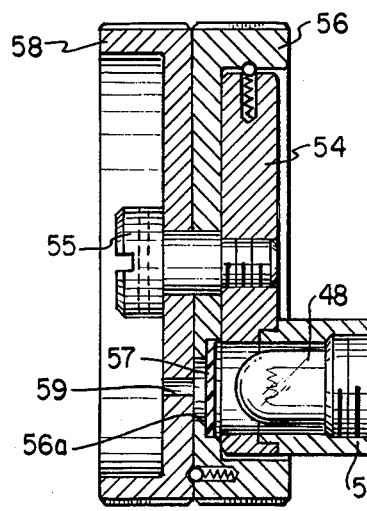
FIG. 7 is an elevational view, partly in cross-section of a portion of one form of light source.

As shown in FIG. 2, a light source 45 is used in association with the instrument to acquire the desired readings. The rear portion of the light source, as seen more clearly in FIG. 7, is of conventional flashlight construction and includes batteries (not shown) within a case 47 having a light bulb 48 at one end thereof. Iris and color filter wheels 56 and 58 are provided on the front end of the light source 45 to select the color and intensity of the light.

The light source 45 is attached to and held at a fixed distance from the center of the cross-piece 32 by a suitable connecting member, such as a thread or string 50. The length of the string 50 is selected, for example, to be 330 mm to make the distance between the light source and the eye substantially equal to that used in the large standard perimeter. Of course, other suitable distances can be used. Thread 50 is preferably made to be detachable from the light source.

FIG. 7 shows further details of the light source. The end of the source containing the light bulb 48 is screwed into a holder 53 which in turn is attached to a plate 54. A screw 56 is threaded into plate 54 to hold the color and iris wheels 56 and 58. Color wheel 56 has a number of openings 56a of substantially equal size, each of which has a standard color filter 57 therein. For example, five holes can be provided in wheel 56 with four filters having the respective colors blue, red, yellow and green. A clear hole (no filter) is also provided. The iris wheel 58 has a number of openings 59 of different sizes therein, for example, ranging from ⅓ mm to 5 mm in diameter. This arrangement enables the ready selection of the test object size and color.

Figure 6A:
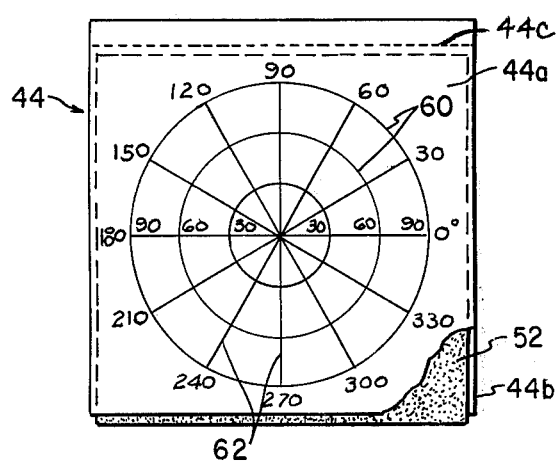
FIGS. 6A and 6B are elevational views of a two part record chart.
Figure 6B:
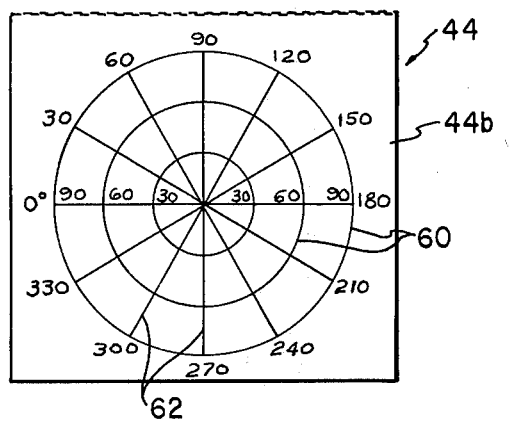

FIGS. 6A and 6B show details of the front and rear sections 44a and 44b of the preferred form of record chart 44. The chart is preferably a two part form with a tear part 44c and is of a suitable size and shape to be held in holder 40. Each part of the two part chart is printed with a number of concentric circles 60 with intersecting angular meridian lines 62. The meridian lines 62 are shown being spaced 30° apart, corresponding to the angular meridian marks 24 on the spectacle frame section 10b. Each point where one of the circles 62 intersects the meridian lines corresponds to an angular mark 29 on the protractor 30. These are shown, for example, as 30° angles on the protractor. Of course, other suitable angular spacing can be used.

The indicia on the bottom, or second part 44b, of chart 44, shown in FIG. 6B, is a mirror image of the top part 44a shown in FIG. 6A. That is, the second part has the meridian angle lines reversed with respect to the first part, for example, the 60° and 120° meridian lines are interchanged as are the 30° and 50° lines. A strip, or sheet, of carbon paper is placed between the two parts of the chart so that when a marking is made on the top part, which is accessible on frame 10 to the examiner, the mark also will appear on the second part through the carbon copy. If desired, instead of using a sheet of carbon paper, a suitable paper with micro-encapsulated carbon can be utilized. Also, instead of using a two part chart, for reasons explained below, a single part chart can be used.

Considering now the operation of the perimeter instrument of the subject invention, reference is made to FIG. 2. The person whose vision is being tested holds the perimeter by handle 18 in the desired position with his eye E in the opening 16 of frame part 10b. The cord 50 is extended to the desired length and the light source 45 energized. The protractor assembly is then turned to align the cross-piece 32 to a desired meridian position. As shown in FIG. 2, it is lying along the 60° – 240° line. The protractor 30 is then rotated to its full out position so that it lies in the same plane as the cross piece which is substantially transverse to the plane of frame 10. The center of the patient's eye will be aligned with the center of the protractor, that is, at 0° on the protractor scale 29. The fixation of the patient's eye is preferably made to take place at the examiner's eye. The light source 45 is moved to various positions with the extended cord 50 resting on or being slightly above perimeter 30. As this is done, the patient is asked for his response to the light source. That is, he is asked to indicate at what point, or angle, as referenced to the protractor scale 29 that the light source disappears from his field of vision. This is done each side of the 0° mark of the protractor with the protractor being aligned on a respective meridian line. The protractor angles at which the patient indicated the light source disappeared are marked on the meridian line of chart top part 44a corresponding to that at which the protractor is aligned.

The foregoing operation is repeated for the same eye E over a number of different meridian positions of the protractor. That is, the protractor is turned to different meridian line positions and the light source moved to different angles with respect to protractor 30. At each meridian position of the protractor, the angle of view measurements are performed by the examiner moving the the light source and the marks are made on the record 44. In this manner, the field of vision is examined over a full 360° (meridian) field and a record thereof made.

When the measurements are completed for one eye, the corresponding two part record chart 44 is removed from holder 40. It should be understood that the charts 44 can be packaged in pad form so that a number of charts are held by holder 40 at one time. The use of the two part chart, with the rear part 44b having mirror image indicia as compared to the first part 44a, gives a record of the patient's subjective representation of the field on the rear part. This leaves a permanent record of the physiological subjective recording of the patient's field as the patient sees it. The information on the front part of the chart is that which was recorded by the examiner.

To examine the patient's other eye, the record holder 40 is removed from frame part 10a, turned around and then replaced. The protractor 30 is rotated about crosspiece 32 through the opening 16. That is, the protractor 30 is rotated anteroposteriorly about the axis of the cross-piece 32. The patient turns the frame 10 around and places opening 16 adjacent his other eye. The field of view measurements are performed again in the manner previously described and recorded on another chart 44.

While a two part chart 44 is preferred, it should be understood that single part charts also can be used. These can be made to record either the subjective field of view as seen by the patient or the objective field of view measured by the examiner.

Figure 8:
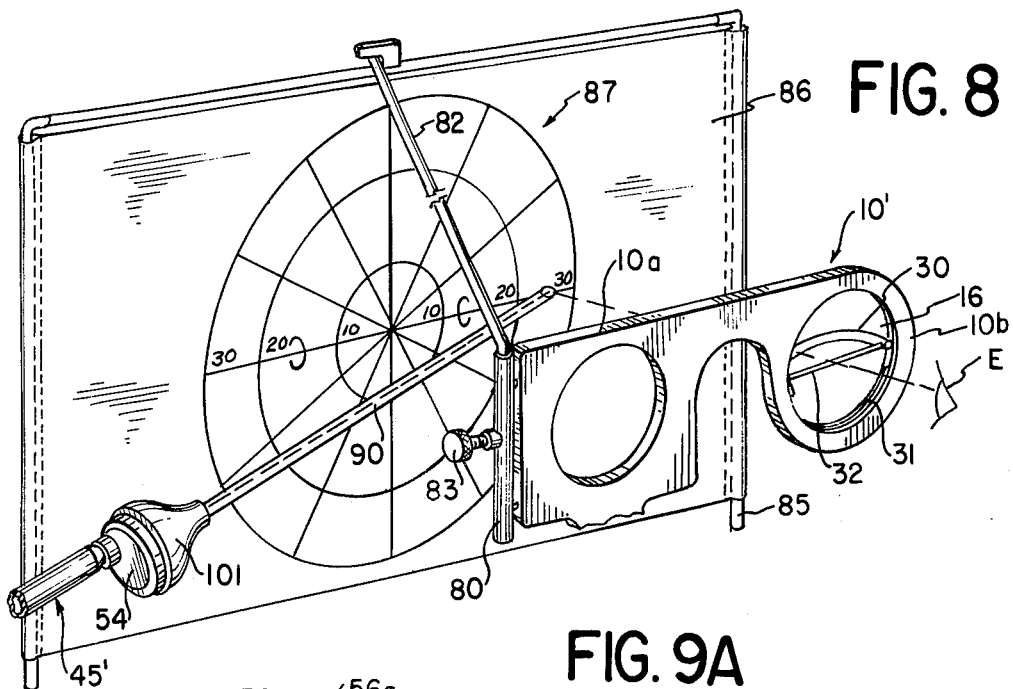
FIG. 8 is a perspective view showing another embodiment of the invention.

FIGS. 8 and 9 show a further modification of the invention in the form of an instrument called a "campimeter". Here, the frame 10' is substantially the same as the frame 10 of the previously described embodiment of the invention with the exception that a tubular mounting member 80 is fastened to the frame section 10a. One leg of a generally L-shaped supporting arm 82 fits within the mounting member and is held by a screw 83. The end of the long leg of the supporting arm holds a frame 85 on which is mounted a screen 86 having a pattern 87 placed thereon by any suitable method, such as by painting, printing, sewing, etc. The length of the long leg of the supporting arm 82 between frame 10' and screen 86 is also preferably selected to be 330 mm although any other suitable length can be utilized. Frame 85 is preferably made to be collapsible and foldable. Similarly, the screen 86 can be rolled or folded so that both the screen and the frame can fit in the examiner's pocket.

The pattern 87 on screen 86 is similar to that on the record medium 44 of FIGS. 1–6. In this embodiment, where the screen 86 is used, the protractor 30 is not rotated but is, instead, maintained fixed in the horizontal plane. Alternately, the protractor portion 30 can be eliminated.

Figure 9A:
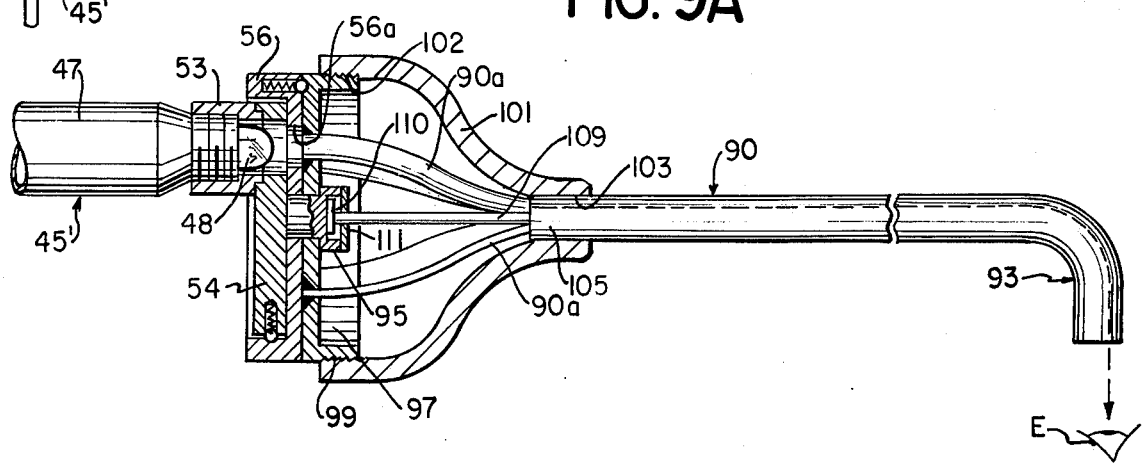
FIG. 9A is an elevational view, partly in cross-section of a portion of a further embodiment of light source for use with the instrument of FIG. 8.
Figure 9B:
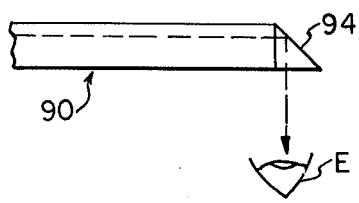
FIG. 9B is an elevational view of a fragment of a modified tip for the light source of FIG. 9A.

The object used to measure the patient's field of view again takes the form of a light source 45' which, in this case, has a light transmitting rod 90 attached thereto. As explained below, rod 90 is composed of a bundle of fibers or rods of different diameters. As shown in FIG. 9A, the rod has a bent end 93 or, as shown in FIG. 9B, it has a prism 94 at its end. Thus, when the end of the rod 90 is placed in front of screen 86 and oriented in the proper direction the light from the source will be directed from the rod 90 toward the eye of the patient. The elongated rod 90 is used so that the hand of the examiner does not have to move in front of the screen 86.

FIG. 9A shows the details of the light source 45' which is, in many respects, similar to that shown in FIG. 7. Here, plate 54 has a hollow headed stud 95 thereon which holds a cup-shaped ring 97 having external threads 99. A bonnet 101 of opaque material with internal threads 102 fastens onto the threads 99 of ring 97. Bonnet 101 has an opening 103 at the end thereof through which the fiber optic bundle 90 passes. The bundle preferably has a light opaque sheath 105 therearound which extends inside the opening 103 of the bonnet. A mounting post 109 extends part way of the length of the bundle and has a head 110 which is rotatable within the head of stud 95 and is held thereto by a plate 110 on the stud.

The post 109 holds a number of fiber optic elements, such as filaments or rods, 90a of different diameters in a fixed position within bonnet 101. The different diameter elements correspond to the various diameter holes of the disc 54 of the light source of FIG. 7. Here, however, the end of each fiber optic element is respectively mounted in a hole on the face of the flange ring 97. As the bonnet 101 and ring 97 are rotated, the different diameter fiber optic elements 90a are brought adjacent a hole 56a on the color wh-el 56 so that the light from bulb 48 is applied to the element 90a adjacent the hold.

As in the case of FIG. 7, wheel 56 has a number of holes 56a with respective color filters and, preferably, a clear hole. The wheel 56 is rotated to provide the desired color light. The size of the object that the patient sees is selectable at will by turning the ring 97 to determine which fiber optic element 90a is to receive light from bulb 48.

In FIG. 9A the end of the fiber bundle 90 is shown as being curved so that the light can be directed directly toward the eye of the patient. In FIG. 9B, a prism 94 is used so that the light will be reflected toward the eye E.

Figure 10:
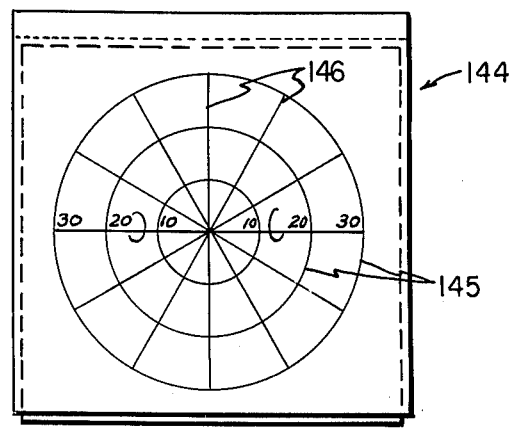
FIG. 10 is a front view of a form of record chart for the instrument of FIG. 8.

FIG. 10 shows the front part of the record chart 144 to be used with the campimeter of FIG. 8. This chart, in single or two part form, is held in the holder 40 which is attached to frame section 10a. The holder 40 is not shown in FIG. 10. The concentric circles 145 on chart 144 correspond to the angle markings on the protractor 30. The angles for the meridian lines 146 are not shown. As before, the record chart 144 is preferably of two parts the first of which is backed with carbon paper. A mirror image of the pattern printed on the first part is printed on the second part. Thus, as the examiner records the information of the patient's response on the front part, the subjective response is available on the second part.

The instrument of FIG. 8 is used in a manner similar to that of FIGS. 1–4. That is, the examiner moves the object, the tip of rod 90, in front of the pattern 87 on screen 86 along one of the meridian lines. No cord 50 is needed since arm 82 maintains frame 10 at a fixed distance from the screen 86. The patient indicates his response with respect to his field of view and the response is marked on the record chart 144. The tip of the rod 90 representing the object is moved along the various meridian lines to obtain the complete field of view response. As should be apparent, the perimeter 30 on the frame 10 is not needed in this case.

FIG. 11 shows a modification of the embodiment of FIG. 8 in which the supporting arm 82 holds a frame 124 having front and rear sections 125 and 127. The pattern 87 (not shown) of FIG. 8 is printed on a screen of light transparent material held by the front section 125 of frame 124. The rear section 127 of the frame has a screen which is of opaque material. The rod 90 of the light source 45', representing the object which the patient's eye is to see, is moved between the two cloths held by frames 125 and 127 and the light is transmitted through the cloth on front frame section 125.

FIG. 12 shows an arrangement similar to that of FIG. 11 in which the opaque rear screen has been omitted. The operation of the embodiments of FIGS. 11 and 12 are the same as that previously described for FIG. 8.

FIG. 13 shows a further embodiment of the light source which is similar in many respects to that of FIG. 7. Here the two dials 56 and 58 are mounted at right angles to the battery holder 47 and lamp 48 by the 90° collar 53a. This arrangement permits the examiner to readily move the light source in front of the screen 86 of FIG. 8 without having his hand in an awkward position as would occur if the light source of FIG. 7 was utilized. The light source of FIG. 13 also can be used with the perimeter instrument of FIGS. 1–5.

What is claimed is:

1. A perimeter instrument for making measurements of the visual field of an eye of a human comprising in combination a frame, said frame formed with an opening therein to accommodate viewing therethrough by the eye whose visual field is to be measured, protractor means, means attached to said frame for holding said protractor means in said opening, said protractor means including a base line portion extending across said opening and a measuring portion for indicating an angular relationship with respect to a point on said base line, a movable object to be viewed by the eye when in said opening, and elongated means connected between said object and said instrument, said elongated means intersecting said point on said base line portion and having a portion thereof lying adjacent said measuring portion of said protractor means, said portion of said elongated means adjacent said measuring portion of said protractor means indicating the angle of said object with respect to the base line portion.

2. The combination of claim 1 further comprising a foldable handle attached to said frame.

3. The combination of claim 1 wherein said measuring portion of said protractor means has markings thereon representative of angles.

4. The combination of claim 1 wherein said mounting means for holding said protractor means includes means for turning said base line portion of said protractor means to a selected meridian angular position across said opening.

5. The combination of claim 1 further comprising indicia marked on said frame to indicate the meridian angular orientation of the base line portion of said protractor means across said opening.

6. The combination of claim 1 wherein said measuring portion of said protractor means has markings thereon representative of angles.

7. The combination of claim 5 wherein said measuring portion of said protractor means has markings thereon representative of angles.

8. The combination of claim 1 wherein said protractor holding means includes means for rotating the measuring portion of said protractor through said opening.

9. The combination of claim 1 further comprising means removably mounted on said frame for holding a record medium thereon.

10. The combination of claim 4 further comprising a record medium mounted on said frame, said record medium including a chart having indicia thereon of a plurality of concentric circles and a number of angular meridian lines corresponding to the meridian portion of the base line portion of said protractor means, said meridian line intersecting at the common center point of the concentric circles.

11. The combination of claim 10 wherein said record medium is a two part chart, the bottom part of the chart having a mirror image of the angular meridian lines which are on the top part, and means for transferring information marked on the top part of the chart to the bottom part.

12. A perimeter instrument as in claim 4 further comprising marks on said measuring portion of said protractor means to indicate an angular relationship with respect to said point on said protractor means base line portion, and marks on said frame adjacent said opening to indicate the meridian to which the base line portion of said protractor means has been rotated.

13. A perimeter instrument as in claim 1 wherein said holding means includes means for holding the measuring portion of said protractor means in a plane which is at an angle to the plane of the opening.

14. A perimeter instrument as in claim 1 wherein said base line portion of said protractor means extends across said opening.

15. A perimeter instrument as in claim 1 wherein said object comprises a light source.

16. The combination of claim 15 wherein said light source includes a light bulb, a first wheel mounted for rotation with respect to said light bulb and having a number of color filters therein to permit light of different colors to be produced.

17. The combination of claim 15 wherein said light source includes a light bulb, a second wheel mounted for rotation with respect to said light bulb and having a number of means of different size to control the intensity of the light output of said source.

18. The combination of claim 15 wherein said light source includes a light bulb, a first wheel mounted for rotation with respect to said light bulb and having a number of color filters therein to permit light of different colors to be produced, and a second wheel mounted for rotation with respect to said light bulb and having a number of means of different size to control the intensity of the light output of said source.

19. A perimeter instrument as in claim 1 further comprising a record medium mounted on a portion of said frame spaced from said opening.

20. A perimeter instrument as in claim 19 wherein said frame is in the general shape of a pair of eyeglasses, said opening being at a position normally occupied by one of the eyeglass lenses and said record medium is located at a position normally occupied by the other of the eyeglass lenses.

21. A perimeter instrument as in claim 1 further comprising a handle, and means for attaching said handle to said frame for pivotal movement of one with respect to the other.

22. An instrument for use in the measurement of the visual field of an eye of a human comprising a frame in the general shape of a pair of eyeglasses, said frame formed with an opening at a position normally occupied by one of the eyeglass lenses, protractor means in said opening for measuring the visual field of an eye looking through said opening, a record medium having indicia thereon corresponding to the visual field and means for mounting said record medium at the position normally occupied by the other of the eyeglass lenses.

23. An instrument for measuring the visual field of an eye of a human comprising in combination, a frame, said frame formed with an opening therein to accommodate viewing therethrough by the eye of whose visual field is to be measured, a foldable screenholder, a first screen of foldable material on said screenholder, said first screen being of foldable material which is at least partially light transmissive and having a predetermined indicia pattern on the front face thereof, a second screen of foldable material on said screenholder spaced from said first screen, an elongated rigid member, means on said frame for supporting one end of said elongated member, means on the other end of said elongated member for attachment to and support of said screenholder to thereby maintain a substantially constant distance and spatial orientation between said screenholder and said frame with the frame supporting the screenholder and the screen thereon, and a light source for viewing by the eye movable between said first and second screens with respect to the indicia pattern.

24. The combination of claim 23 wherein said frame includes means for blocking the eye whose visual field is not being measured, said supporting means on said frame including means for permitting the frame to be turned by 180° while still maintaining said constant distance and spatial orientation.

25. The combination of claim 24 wherein said light source includes an elongated light transmitting member, said light transmitting member having an end portion through which the light from the source exits.

26. The combination of claim 25 wherein said end portion of the elongated light transmitting member is curved to direct light toward the frame.

27. The combination of claim 25 wherein said end portion of the light transmitting member includes a prism to direct the light toward the frame.

* * * * *